United States Patent
Yonce et al.

(10) Patent No.: US 7,113,823 B2
(45) Date of Patent: Sep. 26, 2006

(54) MORPHOLOGY-BASED OPTIMIZATION OF CARDIAC RESYNCHRONIZATION THERAPY

(75) Inventors: David J. Yonce, Fridley, MN (US); David Ternes, Roseville, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 30 days.

(21) Appl. No.: 10/723,255

(22) Filed: Nov. 26, 2003

(65) Prior Publication Data

US 2004/0158293 A1    Aug. 12, 2004

Related U.S. Application Data

(63) Continuation-in-part of application No. 10/003,718, filed on Oct. 26, 2001, and a continuation-in-part of application No. 10/251,629, filed on Sep. 19, 2002.

(51) Int. Cl.
*A61N 1/18*    (2006.01)

(52) U.S. Cl. ............................................. 607/9; 607/15

(58) Field of Classification Search .................... 607/9, 607/15, 27, 28
See application file for complete search history.

(56) References Cited

U.S. PATENT DOCUMENTS

| | | |
|---|---|---|
| 4,832,041 A | 5/1989 | Wang et al. |
| 4,895,152 A | 1/1990 | Callaghan et al. |
| 5,273,049 A | 12/1993 | Steinhaus et al. |
| 5,312,445 A | 5/1994 | Nappholz et al. |
| 5,330,511 A | 7/1994 | Boute |
| 5,331,966 A | 7/1994 | Bennett et al. |
| 5,334,220 A | 8/1994 | Sholder |
| 5,340,361 A | 8/1994 | Sholder |
| 5,350,410 A * | 9/1994 | Kleks et al. .................. 607/28 |
| 5,391,192 A | 2/1995 | Lu et al. |
| 5,458,623 A | 10/1995 | Lu et al. |
| 5,534,016 A | 7/1996 | Boute |
| 5,626,623 A | 5/1997 | Kieval et al. |
| 5,660,184 A | 8/1997 | Donehoo et al. |
| 5,674,254 A | 10/1997 | van Krieken |
| 5,741,308 A | 4/1998 | Sholder |
| 5,755,739 A | 5/1998 | Sun et al. |
| 5,771,898 A | 6/1998 | Marinello |
| 5,778,881 A | 7/1998 | Sun et al. |
| 5,782,888 A | 7/1998 | Sun et al. |
| 6,029,088 A | 2/2000 | Budgifvars et al. |
| 6,101,416 A | 8/2000 | Sloman |
| 6,128,535 A * | 10/2000 | Maarse ........................ 607/28 |
| 6,169,921 B1 | 1/2001 | KenKnight et al. |

(Continued)

FOREIGN PATENT DOCUMENTS

WO    WO-2004026398 A1    4/2004

*Primary Examiner*—George Manuel
*Assistant Examiner*—Lenwood Faulcon, Jr.
(74) *Attorney, Agent, or Firm*—Schwegman, Lundberg, Woessner & Kluth, P.A.

(57) ABSTRACT

A method and apparatus for delivering cardiac resynchronization therapy (CRT) in which an evoked response electrogram is recorded during one or more cardiac cycles and used to aid in the selection of resynchronization pacing parameters and/or to monitor the effectiveness of resynchronization therapy. The morphology of an evoked response electrogram may be recorded and analyzed to determine if and when intrinsic activation of one ventricle is occurring in order to optimally adjust the programmed atrio-ventricular (AV) delay interval for ventricular resynchronization pacing of a patient with intact AV node conduction.

20 Claims, 4 Drawing Sheets

U.S. PATENT DOCUMENTS

| | | | |
|---|---|---|---|
| 6,456,881 B1 * | 9/2002 | Bornzin et al. | 607/27 |
| 6,512,953 B1 | 1/2003 | Florio et al. | |
| 6,697,673 B1 * | 2/2004 | Lu | 607/28 |
| 6,738,669 B1 * | 5/2004 | Sloman et al. | 607/28 |
| 6,829,505 B1 | 12/2004 | Kramer et al. | |
| 2001/0049543 A1 * | 12/2001 | Kroll | 607/28 |
| 2003/0083710 A1 | 5/2003 | Ternes et al. | |
| 2003/0083711 A1 | 5/2003 | Yonce et al. | |
| 2004/0158165 A1 | 8/2004 | Yonce et al. | |

* cited by examiner

MORPHOLOGY-BASED OPTIMIZATION OF CARDIAC RESYNCHRONIZATION THERAPY

RELATED APPLICATIONS

This application is a continuation-in-part of U.S. patent application Ser. Nos. 10/003,718, filed on Oct. 26, 2001 and 10/251,629, filed on Sep. 19, 2002 the disclosures of which are hereby incorporated by reference in their entirety.

FIELD OF THE INVENTION

This patent application pertains to methods and apparatus for the treatment of cardiac disease. In particular, it relates to methods and apparatus for improving cardiac function with resynchronization therapy.

BACKGROUND

Implantable devices that provide electrical stimulation to selected chambers of the heart have been developed in order to treat a number of cardiac disorders. A pacemaker, for example, is a device which paces the heart with timed pacing pulses, most commonly for the treatment of bradycardia where the ventricular rate is too slow. Atrio-ventricular conduction defects (i.e., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Implantable devices may also be used to treat cardiac rhythms that are too fast, with either anti-tachycardia pacing or the delivery of electrical shocks to terminate atrial or ventricular fibrillation.

Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways, such as bundle branch blocks, can thus suffer compromised pumping performance.

Heart failure refers to a clinical syndrome in which an abnormality of cardiac function causes a below normal stroke volume that can fall below a level adequate to meet the metabolic demand of peripheral tissues. It usually presents as congestive heart failure (CHF) due to the accompanying venous and pulmonary congestion. Heart failure can be due to a variety of etiologies with ischemic heart disease being the most common. Some heart failure patients suffer from some degree of AV block or are chronotropically deficient such that their cardiac output can be improved with conventional bradycardia pacing. Such pacing, however, may result in some degree of uncoordination in atrial and/or ventricular contractions because pacing excitation from a single pacing site is spread throughout the myocardium only via the much slower conducting muscle fibers of either the atria or the ventricles, and not the specialized conduction pathways. Most pacemaker patients can still maintain more than adequate cardiac output with artificial pacing, but the diminishment in pumping efficiency may be significant in a heart failure patient whose cardiac output is already compromised. Intraventricular and/or interventricular conduction defects are also commonly found in heart failure patients and can contribute to cardiac dysfunction by causing unsynchronized contractions during intrinsic beats. Other conduction defects can occur in the atria.

In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization results in a more coordinated contraction of the ventricles with improved pumping efficiency and increased cardiac output. Currently, a most common form of CRT applies stimulation pulses to both ventricles, either simultaneously or separated by a specified biventricular offset interval, and after a programmed atrio-ventricular (AV) delay interval with respect to the detection an intrinsic atrial contraction or delivery of an atrial pace. Appropriate specification of these parameters is necessary in order to achieve the desired optimum coordination between the atria and the ventricles and within the ventricles, and it is this problem with which the present invention is primarily concerned.

SUMMARY

The present invention relates to methods and apparatus for delivering cardiac resynchronization therapy (CRT) in which an evoked response electrogram is recorded during one or more cardiac cycles and used to aid in the selection of resynchronization pacing parameters and/or to monitor the effectiveness of resynchronization therapy. Analysis of the morphology of evoked response electrograms may be used to maintain optimum hemodynamics by comparing recorded evoked response electrograms with a template waveform representative of the optimum situation and adjusting one or more pacing parameters accordingly. Examples of pacing parameters which may be adjusted in accordance with a morphology-based algorithm include the pacing pulse energy, the atrio-ventricular (AV) interval for atrial tracking and AV sequential pacing modes, the biventricular offset interval for biventricular pacing modes, and the particular pacing mode to be used for delivering cardiac resynchronization therapy.

In one particular embodiment, the morphology of an evoked response electrogram is recorded and analyzed to determine if and when intrinsic activation of the right ventricle is occurring in order to optimally adjust the programmed atrio-ventricular (AV) delay interval for biventricular or left ventricle-only (LV-only) resynchronization pacing of a patient with intact AV node conduction. Analysis of the morphology of recorded evoked response electrograms can also be used to optimally adjust the AV delay of a conventional dual-chamber pacemaker in which only one ventricle is paced. In another embodiment, morphology analysis is used to aid in monitoring the patient's condition by logging significant changes made to pacing parameters by morphology-based algorithms and/or by classifying evoked response electrograms into different events based upon their morphology and maintaining counts of each type of event.

DETAILED DESCRIPTION

Figure 1:
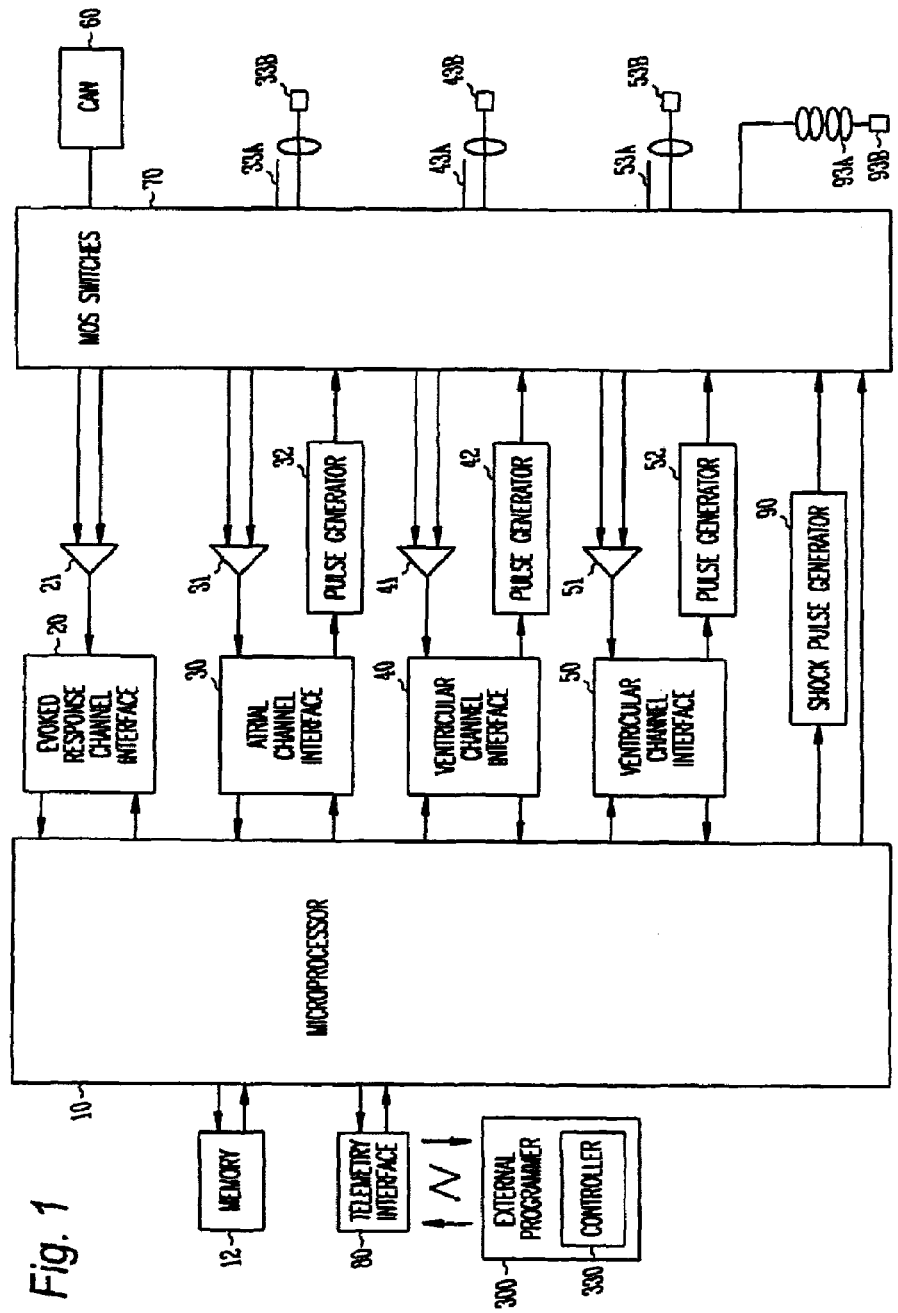
FIG. 1 is a system diagram of an exemplary CRT device.

Cardiac devices configured for delivering resynchronization or other pacing therapy may be programmed with a number of different parameter settings that affect the patient's cardiac performance. In a biventricular pacing mode, for example, pacing pulses may be delivered to the right and left ventricles during a cardiac cycle with a specified offset interval between the pulses designed to produce a synchronized contraction within the left ventricle and between both ventricles. Because of different conduction conditions in the two ventricles, the optimum offset interval for producing a synchronized, and hence more efficient, left ventricular contraction in a given patient may vary. Another parameter that affects cardiac performance is the atrio-ventricular (AV) delay interval used in atrial tracking modes, which may be employed for resynchronization as well as conventional bradycardia pacing. In an atrial tracking mode, the ventricles are stimulated following an atrial intrinsic contraction or atrial pace so that diastolic filling is augmented prior to ventricular systole. The optimum values for these CRT parameters as well as others which affect CRT performance vary not only from patient to patient but may also change over time in an individual patient. For example, the optimum value for the atrio-ventricular interval varies with heart rate and from patient to patient. It would be desirable for a cardiac resynchronization device to possess a means of monitoring CRT performance so that CRT parameters can be adjusted accordingly, either manually via an external programmer or automatically in accordance with an algorithm programmed into the device. The present invention relates to methods and apparatus for accomplishing this objective by analyzing the morphology of evoked response electrograms which show the time course of cardiac depolarization during a paced cycle as sensed by an electrode. Such electrograms are referred to herein as test electrograms. The morphology of such an evoked response electrogram may be analyzed by comparing it with a template representing the optimum or desired situation, where the comparison is performed by, for example, cross-correlating the test electrogram with the template or comparing identifiable features of the test electrogram and template waveforms. One or more pacing parameters may then be adjusted in a manner which would tend to make a subsequent test electrogram conform to the template. Among the pacing parameters which may be adjusted in this manner are the pacing pulse energy, the pacing mode, the atrio-ventricular delay interval, and the biventricular offset interval.

One aspect of CRT performance which can be ascertained by morphology analysis of an evoked response electrogram is whether or not the pace or paces delivered during a cardiac cycle have succeeded in capturing the heart, where capturing refers to causing sufficient depolarization of the myocardium that a propagating wave of excitation and contraction result. In order for a pacing pulse to capture the heart, it must have sufficient energy, and it is desirable to minimize pacing pulse energy as much as possible while still providing reliable pacing. The use of morphology analysis of evoked response electrograms for capture verification and automatic adjustment of pacing pulse energy (referred to as autocapture) is described in U.S. patent application Ser. No. 10/251,629 where a test evoked electrogram recorded during a CRT pacing cycle is compared against templates representing biventricular (BiV) capture, right ventricle-only (RV-only) capture, and left ventricle-only (LV-only) capture.

Besides pacing pulse energy, another factor which affects whether and to what extent a pacing pulse captures the heart is intrinsic cardiac activity. If a pace is delivered to a cardiac chamber shortly after intrinsic excitation of the chamber during the refractory period, no further excitation occurs from the pace. If a pace is delivered to a cardiac chamber while the chamber is depolarizing from intrinsic excitation, a fusion beat results. The morphologies of evoked response electrograms recorded during such fusion beats and refractory paces are different from the morphologies of electrograms recorded during paces which result in true capture. This can present a problem to devices employing a template-based autocapture system because fusion beats and refractory paces may be falsely interpreted as indicative of insufficient pacing pulse energy. (Threshold autocapture systems may also falsely interpret fusion beats.) It is therefore desirable for the timing of pacing pulses to be adjusted in a manner which prevents interference with paces by intrinsic activity. For example, the programmed AV delay interval may be selected as a fixed value that is much shorter than the patient's intrinsic AV interval. If the programmed AV delay interval is short enough so that excitation resulting from a pace always reaches the ventricular sensing site where the evoked response electrogram is recorded before the intrinsic excitation has time to propagate to that site from the AV node, such evoked response electrograms will not change as the intrinsic AV interval varies with heart rate. For example, in the case of biventricular pacing cycles where there is a loss of capture in the right ventricle, evoked response electrograms recorded from the right ventricle during such cycles are invariant with respect to changes in the patient's intrinsic AV interval as long as the programmed AV delay interval is shorter than the patient's intrinsic AV interval by a margin at least greater than the time it takes for excitation to propagate from the paced left ventricle to the right ventricle.

A disadvantage of a fixed programmed AV delay interval, however, is that the hemodynamically optimum value for this parameter varies with rate. The heart rate in a normal individual increases in response to increased metabolic demand or emotional excitement due to hormonal and neural influences, the latter being increased sympathetic discharge relative to parasympathetic discharge. The neural and hormonal influences responsible for the increased heart rate also increase the force of cardiac contractions and decrease the intrinsic AV interval since the ventricles need to be filled more rapidly during a shorter diastole if cardiac output is to be increased. For optimum hemodynamics, an implanted pacemaker delivering either bradycardia or CRT ventricular pacing should vary the pacing rate and programmed AV delay interval in accordance with metabolic demand in a manner that mimics the normal physiological situation. In a chronotropically competent patient, the ventricular pacing rate can be varied in accordance with metabolic demand through the use of an atrial tracking mode in which the patient's natural atrial rhythm controls the ventricular pacing rate. In a chronotropically incompetent patient, rate-adaptive pacing modes can be employed in which the atrial and ventricular pacing rate is controlled by a measured parameter reflective of metabolic demand such as activity level or minute ventilation. In either case, an implanted device can be programmed to vary its programmed AV delay interval along with the ventricular pacing rate in a manner which maintains optimum hemodynamic performance. This means that the programmed AV delay interval should match the patient's intrinsic AV interval, where "match" in this case may mean that the programmed AV delay interval is always slightly shorter than the intrinsic AV interval so that intrinsic excitation from the AV node does not affect evoked response electrograms recorded during ventricular pacing in patients with an intact AV conduction pathway. An empirically derived look-up table or other mapping function can be employed by the implantable device to map particular ventricular pacing rates to programmed AV delay intervals that are matched to the optimum.

Determining how a patient's intrinsic AV interval varies with either the natural atrial rhythm or with the output of a metabolic demand sensor such as an accelerometer or minute ventilation sensor, however, is problematic. Moreover, in any particular patient, the manner in which the intrinsic AV interval varies may change over time. It would therefore be useful for an implanted device to have the capability of detecting when the programmed AV delay interval does not match the patient's intrinsic AV interval and automatically adjusting the programmed AV delay interval so that it does match. In one embodiment of the present invention, an implantable CRT device is programmed to adjust the programmed AV delay from recorded evoked response electrograms. Such morphology-based adjustment of the programmed AV delay may be implemented in biventricular as well as conventional dual-chamber pacing modes. The AV delay adjustment algorithm involves comparison of an evoked response electrogram with a template representing capture of a ventricle or ventricles by a pacing pulse or pulses delivered at an AV delay interval assumed to be optimum. The AV delay is then adjusted in a manner which causes the evoked response electrogram to more nearly resemble the template.

One application of the morphology-based algorithm described above is to optimize the AV delay interval for delivering CRT which requires nearly 100% pacing of the ventricles to be effective. A morphology-based AV delay optimization algorithm can also work to vary the AV delay to maintain the ventricular morphology with rate. For instance, a rate increase in a heart failure patient causes the intrinsic AV delay to shorten. If the programmed AV delay was not short enough at the new rate, intrinsic conduction would take over in the RV, reducing the benefit of CRT. By optimizing the AV delay, this situation can be prevented so that biventricular pacing is always maintained. AV delay optimization may also be employed in a standard dual chamber pacemaker (i.e., a device which paces one atrium and one ventricle). For instance, in a chronotropically competent patient, where the intrinsic AV delay is just shorter or the same as the programmed AV delay, the optimization algorithm could be utilized to recognize this case and potential fusion beats. A dynamic AV delay interval (i.e., one that is made to vary with rate) could be extended (within a boundary) to promote intrinsic conduction and to conserve energy. In this manner, the dynamic AV delay could be tailored to each patient, rather than having the dynamic AV delay that comes programmed in the device be an average of the AV delay response with rate from a study population. Additionally, as it may be beneficial to promote ventricular pacing in some patients; the AV delay optimization algorithm can insure this occurs.

An example of a morphology-based method for adjusting the AV delay interval in a biventricular pacing situation is as follows. In order to more sensitively detect intrinsic activation of the right ventricle, a template electrogram is recorded during an LV-only pace with a programmed AV delay interval known to be matched to the patient's intrinsic AV interval. Periodically and/or at times when the patient's intrinsic AV interval is expected to have changed (e.g., when the patient's intrinsic heart rate changes from that which was present when the template electrogram was recorded), the device records a test electrogram during an LV-only pace and compares it with the template electrogram. In the case where the evoked response electrograms are recorded by an electrode in the right ventricle (such as a shock electrode also used for delivering defibrillation shocks), a peak in the evoked response electrogram of an LV-only pace represents activation of the right ventricle via either intrinsic conduction from the AV node or the spread of excitation from the paced left ventricle. The comparison then involves determining when the peaks in the test and template electrograms occur relative to the pace. If the peak in the test electrogram occurs earlier than the peak in the template, it implies that intrinsic activation of the right ventricle from the AV node is occurring and that the programmed AV delay interval should be shortened if it is to match the intrinsic AV interval. Conversely, if the peak in the test electrogram occurs later than the peak in the template, it implies that the right ventricle is activated by the spread of depolarization from the paced left ventricle before intrinsic excitation can arrive from the AV node and that the programmed AV delay interval should be lengthened in order to match the intrinsic AV interval. (It should be appreciated that the technique could also be applied using an RV-only pace with left ventricular sensing.) In a further refinement, the device determines matched programmed AV delay intervals in this manner for a plurality of different pacing rates (as dictated by the patient's natural atrial rhythm in the case of atrial tracking pacing modes or by sensed exertion levels in the case of rate-adaptive pacing modes). The matched AV delay intervals may then be used to form a look-up table or other function for mapping particular pacing rates to particular programmed AV delay intervals. When the ventricular pacing rate changes, the device may then automatically adjust the programmed AV delay interval accordingly.

Monitoring the morphology of evoked response electrograms recognizing changes to that morphology over time can also be useful in providing improved CRT delivery by allowing the user to re-optimize pacing parameters or perform some other adjustment to therapy based on analysis of this information. Such monitoring may be implemented, for example, by: 1) logging significant changes made to pacing parameters by morphology-based algorithms, 2) maintaining counts of BiV capture, RV-only capture on a BiV pace LV-only capture on a BiV pace, fusion, and no capture, and comparing these evoked response classification counts against a threshold for automatic triggering of a CRT Monitor or other alarm, 3) triggering of user notification based on long-term changes in capture morphology, 4) triggering of electrogram storage, along with storage of other concurrent data such as accelerometer activity, based on changes in capture morphology which may provide information such as that the current programmed CRT is not optimal at elevated rates, and 5) monitoring during automatic adjustment to the programmed left ventricular protection period (LVPP) to ensure that optimal CRT is delivered while maintaining the safety provided by LVPP. The LVPP is a period during which pacing of the left ventricle is inhibited and is used in biventricular or left ventricle-only pacing modes which are based upon right ventricular sensing. Morphology-based algorithms can also be used to determine whether the LVPP is being invoked by true intrinsic depolarization or by far-field sensing. (See U.S. patent application Ser. No. 09/748,754, herein incorporated by reference, for a fuller description of the left ventricular protection period.)

A description of an exemplary cardiac rhythm management device suitable for delivering CRT therapy and recording evoked response electrograms is set forth below. The techniques for optimizing and monitoring CRT performance discussed above may be implemented by appropriate programming of the device's controller. Descriptions of specific embodiments employing those techniques are also given.

1. Exemplary Device Description

Cardiac rhythm management devices such as pacemakers and ICDs are typically implanted subcutaneously on a patient's chest and have leads threaded intravenously into the heart to connect the device to electrodes used for sensing and delivery of electrical stimulation such as defibrillation shocks and pacing pulses. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above the capture threshold must be delivered to the chamber.

A system diagram of an exemplary cardiac rhythm management device for delivering cardiac resynchronization therapy is illustrated in FIG. 1. The controller of the device is made up of a microprocessor 10 communicating with a memory 12, where the memory 12 may comprise a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the device in a number of programmed modes where a programmed mode defines how pacing pulses are output in response to sensed events and expiration of time intervals. A telemetry interface 80 is provided for communicating with an external programmer 300. The external programmer is a computerized device with a controller 330 that can interrogate the device and receive stored data as well as adjust various operating parameters.

The device has an atrial sensing/pacing channel comprising ring electrode 33a, tip electrode 33b, sense amplifier 31, pulse generator 32, and an atrial channel interface 30 which communicates bidirectionally with a port of microprocessor 10. The device also has two ventricular sensing/pacing channels that similarly include ring electrodes 43a and 53a, tip electrodes 43b and 53b, sense amplifiers 41 and 51, pulse generators 42 and 52, and ventricular channel interfaces 40 and 50. For each channel, the electrodes are connected to the pacemaker by a lead and used for both sensing and pacing. A MOS switching network 70 controlled by the microprocessor is used to switch the electrodes from the input of a sense amplifier to the output of a pulse generator. The device also includes a shock pulse generator 90 interfaced to the controller and a shock lead which incorporates a tip electrode 93b and a coil electrode 93a. Coil electrodes can be used to deliver pacing pulses but are designed especially for delivering cardioversion/defibrillation shocks. The shock lead would normally be disposed in the right ventricle (RV) so that sensing or pacing of the ventricles may be performed using tip electrode 93b and/or coil electrode 93a. A ventricular cardioversion/defibrillation shock may be delivered between coil 93a and the can 60 when fibrillation or other tachyarrhythmia is detected. The device also has an evoked response sensing channel that comprises an evoked response channel interface 20 and a sense amplifier 21 that has its differential inputs connected to a selected electrode and to the device housing or can 60 through the switching network 70. The evoked response sensing channel may be used to verify that a pacing pulse has achieved capture of the heart in a conventional manner or, as explained below, used to record an evoked response electrogram.

The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or adjusting the pacing pulse energy by changing the pulse amplitude or pulse width. The microprocessor 10 controls the overall operation of the device in accordance with programmed instructions stored in memory. The sensing circuitry of the device generates atrial and ventricular sense signals when voltages sensed by the electrodes exceed a specified threshold. The controller then interprets sense signals from the sensing channels and controls the delivery of paces in accordance with a programmed pacing mode. The sense signals from any of the sensing channels of the pacemaker in FIG. 1 can be digitized and recorded by the controller to constitute an electrogram that can either be analyzed by the device itself or transmitted via the telemetry link 80 to the external programmer 300.

As described above, CRT involves applying stimulus pulses to one or more heart chambers in a manner that restores or maintains synchronized contractions of the atria and/or ventricles and thereby improves pumping efficiency. Certain patients with conduction abnormalities may experience improved cardiac resynchronization with conventional single-chamber or dual-chamber bradycardia pacing. For example, a patient with left bundle branch block may have a more coordinated contraction of the ventricles with a stimulus pulse than as a result of an intrinsic contraction. More commonly, however, resynchronization therapy involves stimulating both ventricles in order to achieve better intra-ventricular and inter-ventricular synchronous contraction. Better intra-ventricular and inter-ventricular synchronization may be accomplished in a biventricular resynchronization mode by stimulating one ventricle at a specified biventricular offset interval with respect to a stimulus or sense occurring in the contralateral ventricle, the latter being stimulated with a atrial tracking mode or not stimulated at all. For example, if the patient has left bundle branch block (LBBB), in which the left ventricle is activated much later than the right ventricle during an intrinsic beat, synchronization can be restored by pacing the right and left ventricles either simultaneously or at a specified offset interval.

CRT may be most conveniently delivered in conjunction with a bradycardia pacing mode. Bradycardia pacing modes refer to algorithms used to stimulate the atria and/or ventricles when the intrinsic atrial and/or ventricular rate is inadequate due to, for example, AV conduction blocks or sinus node dysfunction. Such modes may involve either single-chamber stimulation, where either an atrium or a ventricle is stimulated, or dual-chamber stimulation in which both an atrium and a ventricle are stimulated. A bradycardia pacing mode can enforce a minimum heart rate either asynchronously or synchronously. In an asynchronous pacing mode, the heart is stimulated at a fixed rate irrespective of intrinsic cardiac activity. There is thus a risk with asynchronous stimulation that a stimulus pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a stimulus pulse. Inhibited demand stimulation modes utilize escape intervals to control stimulation in accordance with sensed intrinsic activity. In an inhibited demand mode, a stimulus pulse is delivered to a heart chamber during a cardiac cycle only after expiration of a defined escape interval during which no intrinsic beat by the chamber is detected. If an intrinsic beat occurs during this interval, the heart is thus allowed to "escape" from stimulation by the device. Such an escape interval can be defined for each stimulated chamber. For example, a ventricular escape interval can be defined between ventricular events so as to be restarted with each ventricular sense or stimulation. The inverse of this escape interval is the minimum rate at which the device will allow the ventricles to beat, sometimes referred to as the lower rate limit (LRL).

In atrial tracking modes, another ventricular escape interval is defined between atrial and ventricular events, referred to as the programmed AV delay interval. The programmed AV delay interval is triggered by an atrial sense or stimulus and stopped by a ventricular sense or stimulus. A ventricular stimulus pulse is delivered upon expiration of the AV delay interval if no ventricular sense occurs before. Atrial-tracking stimulation of the ventricles attempts to maintain the atrioventricular synchrony that occurs with physiological beats whereby atrial contractions augment diastolic filling of the ventricles. As noted above, the value of the programmed AV delay interval for optimal preloading of the ventricles will vary from patient to patient and also varies with heart rate.

The electrical response of the heart to a pacing pulse is referred to as an evoked response. If the evoked response indicates that a propagating wave of depolarization has resulted from the pacing pulse, it evidences that the paced chamber has responded appropriately and contracted. An evoked response can therefore be used to verify that the pace has achieved capture of the heart. An electrogram can also be recorded of an evoked response to a pace and used to determine if capture is achieved by comparing the recorded electrogram with a template electrogram representing capture of the heart by a similarly delivered pace. An evoked response sensing channel for recording an electrogram can be a sensing channel normally used for other purposes or can be a sensing channel dedicated to sensing evoked responses. In the embodiment illustrated in FIG. 1, a dedicated evoked response sensing channel is provided where the differential inputs of sensing amplifier 21 may be connected to a selected electrode and the can 60 by means of switch matrix 70. An electrogram signal for morphology analysis is preferably obtained from a unipolar electrode with a large surface area rather than a conventional bipolar sensing/pacing electrode. A large unipolar electrode "sees" a larger volume of the myocardium, and changes in the depolarization pattern of the ventricles will be more readily reflected in an electrogram generated by the electrode during a ventricular beat. A convenient electrode for this purpose is the coil electrode that the device normally uses for delivering cardioversion/defibrillation shocks. The sensing channel incorporating the shock electrode and which is used to generate electrograms for morphology analysis is referred to herein as the shock channel.

2. Morphology-based Pacing Parameter Adjustment to Maintain Optimum Hemodynamics There are a number of methods which can be used to determine pacing parameters for bradycardia pacing or CRT which yield optimal hemodynamics including echocardiograms, pulmonary capillary wedge pressure (PCWP) measurements, and correlation of parameters with pulse pressure optimization. A general limitation of each of these methods is that they are performed while the patient is at rest and in a sitting or prone position. The pacing settings that provide the physiologically optimal hemodynamics at rest may not provide the same optimal hemodynamics when the patient is active or even standing. Factors such as change in autonomic tone can come into play. Also, optimal pacing settings may change over time, and the aforementioned methods are difficult to implement as automatic algorithms executable by an implanted device. The present invention makes use of the fact that the electrical morphology of the paced evoked response correlates to optimal hemodynamics. That is, for a given patient there is a correlation between the electrical morphology of the evoked response electrogram and whether or not physiologically optimal hemodynamics are being achieved. An algorithm executable by the implanted device can thus maintain optimal hemodynamics over a range of activity and heart rate by modifying pacing parameters so that the morphology of evoked response electrograms is the same or similar to the morphology of a template, where the template may be an evoked response electrogram obtained when optimal hemodynamics are known to be present as determined by other means such as the methods noted above. In an exemplary method for setting the pacing parameters of a cardiac rhythm management device implanted in a patient, a pacing parameter is set to a plurality of different values while assessing the patient's hemodynamic performance in order to determine an optimum value which results in the best hemodynamic performance. The pacing parameter is then set to the optimum value, an evoked response electrogram is recorded during delivery of a pace, and the recorded electrogram is stored as a template. Subsequently, during normal operation of the device, test evoked response electrograms are recorded during one or more cardiac cycles, and their morphologies are compared. The value of the pacing parameter is then automatically adjusted by the device so that the morphology of a subsequently recorded test electrogram will more nearly resemble the morphology of the template.

In one example implementation, a clinician first determines the pacing parameters that provide the most physiologically optimal hemodynamics for a specific patient. This determination may be based on input from commonly accepted practices for assessing hemodynamics. The clinician thus manually reprograms the pacing parameters to obtain results from echocardiograms or PCWP for a range of programming options. Once the clinician determines the optimal configuration, the clinician instructs the device to store the paced evoked response electrogram as a template.

Alternatively, an external programmer may execute an algorithm for automatic setting of pacing parameters, with the evoked response resulting from the optimized pacing parameters automatically stored as the template by the device. For example, the external programmer may automatically control the reprogramming of AV delay, biventricular offset, or whatever pacing parameter is being optimized. The programmer could pace at each setting for a predetermined number of cardiac cycles (e.g., 10) or for a predetermined time (e.g., 10 ms), or it could hold at the current pacing parameter settings until the clinician instructs the programmer to go to the next step. After the number of pacing parameters settings are exhausted, the implantable device is programmed to the settings determined as optimal. In one embodiment, the implantable device stores the evoked response morphology at each setting, and these morphologies are displayed to the clinician so that the clinician can select which one, in his or her estimation, represents the optimal morphology. The device then automatically programs the pacing parameters associated with that morphology and uses that morphology as its definition of "optimal" (i.e., as a template). Another option is for the clinician to instruct the programmer that the current pacing parameters under test are the optimal ones. The programmer then automatically reprograms the implantable device to those values with the evoked response morphology representing the "optimal" morphology stored as a template.

In another embodiment, the implantable device automatically determines from all of the stored evoked response morphologies which evoked response morphology is the optimal. The device then automatically sets its pacing parameters to the parameter values associated with that morphology and uses that morphology as its definition of "optimal" (i.e., as a template). The steps to determine the optimal pacing parameters could be done on an automatic basis such as daily, monthly, or triggered by sensed conditions. The automatic determination of which evoked response morphology is optimal could be based on criteria such as area under the evoked response morphology curve, width of evoked response, time to peak of evoked response after pace. Automatic updates may be of a benefit since optimal pacing parameters may change due to remodeling of the heart, change in physical condition, change in drug regimen, and other factors.

3. Example Algorithm for Optimal Adjustment of Programmed AV Delay Interval

Figure 2:
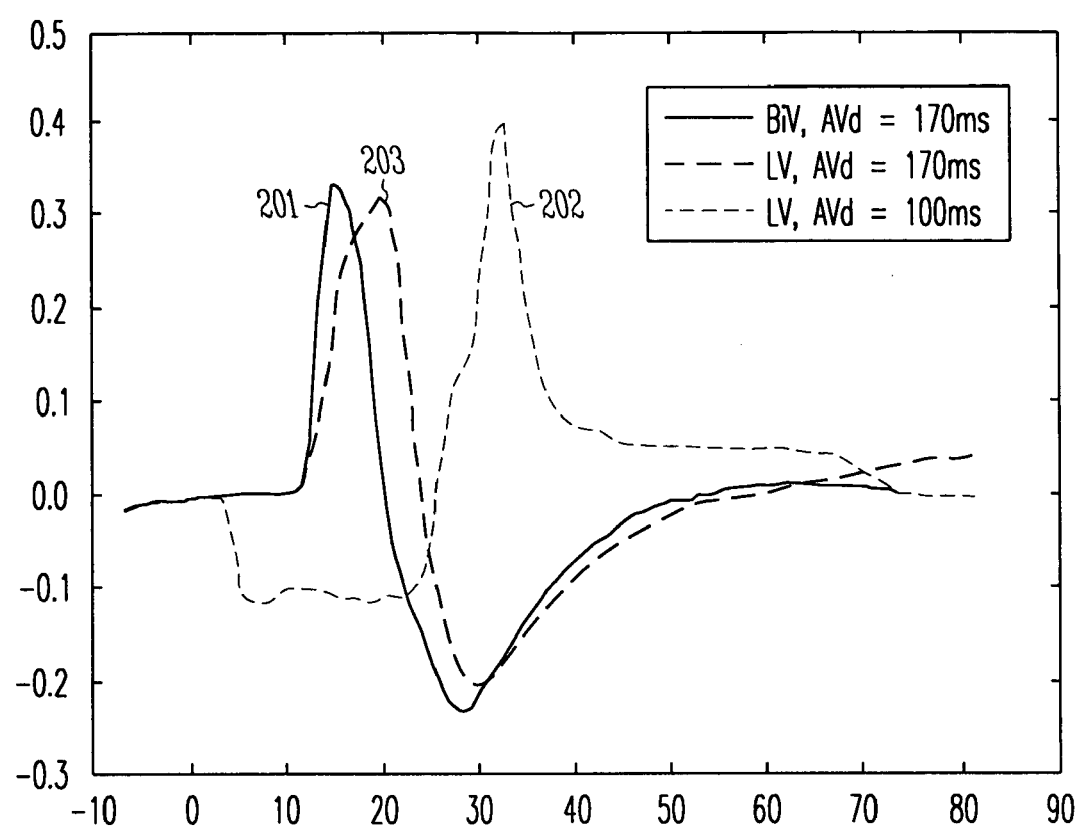
FIG. 2 shows an example evoked response electrograms.

The programmed AV delay interval setting can cause significant morphology changes and possibly create errors in a template-based capture determination algorithm. This effect is most significant when sensing an LV-only morphology from the right ventricle. FIG. 2 shows a BiV evoked response 201 and an LV-only evoked response 202 with different AV delay intervals as recorded from the right ventricular shock channel. First, consider the case with a loss of RV capture (LV-only pacing) where the programmed AV delay interval is much shorter than the intrinsic AV interval. Ventricular paces then occur in both ventricular chambers, but the device only captures the left side of the heart. The depolarization wavefront then propagates from the left ventricle to the right ventricle, causing a peak in the evoked response electrogram when the depolarization wavefront reaches the cardiac tissue near the shock sensing coils. This tissue also enters a refractory state allowing no further ventricular activity from any intrinsic signals propagating through the AV node. This results in an LV-only evoked response much different from a BiV response, as shown by comparing waveforms 201 and 202 in FIG. 2. Alternatively, consider a similar loss of RV capture, but with the AV delay interval programmed very near the intrinsic AV interval. A BiV pace again only captures the left side of the heart, but because of the small difference between the intrinsic and programmed AV delays, the intrinsic signal propagating through the AV node depolarizes the right ventricle tissues before the wavefront arrives from the left side. This results in a much earlier peak in the LV-only evoked response 203, more closely resembling the BiV response 201. In this case, the device is essentially operating in a BiV-triggered mode.

These scenarios illustrate the errors that can be induced in template matching if the programmed AV delay interval does not match the intrinsic delay. This becomes especially important in an ambulatory setting where the patient's pacing rate and intrinsic AV delay may change. Programming the AV delay much shorter than the intrinsic value during a threshold test provides one solution. In that case, the evoked response morphology is invariant if the difference between the intrinsic AV interval $AV_i$ and the programmed AV delay interval $AVD_p$ is greater than the time it takes the depolarization wavefront to propagate from the left to right ventricle $t_{LV \to RV}$:

$$AV_i - AVD_p > t_{LV \to RV}$$

A dynamic AV delay is preferable for optimum hemodynamics, but only if the dynamic changes closely match the patient's intrinsic AV delay variations will invariance in evoked response morphology be maintained. This presents an opportunity to optimize the dynamic AV delay for each particular patient; the degree of similarity of LV-only responses sensed from the right ventricle at different rates indicates the accuracy of the dynamic AV delay.

Figure 3:
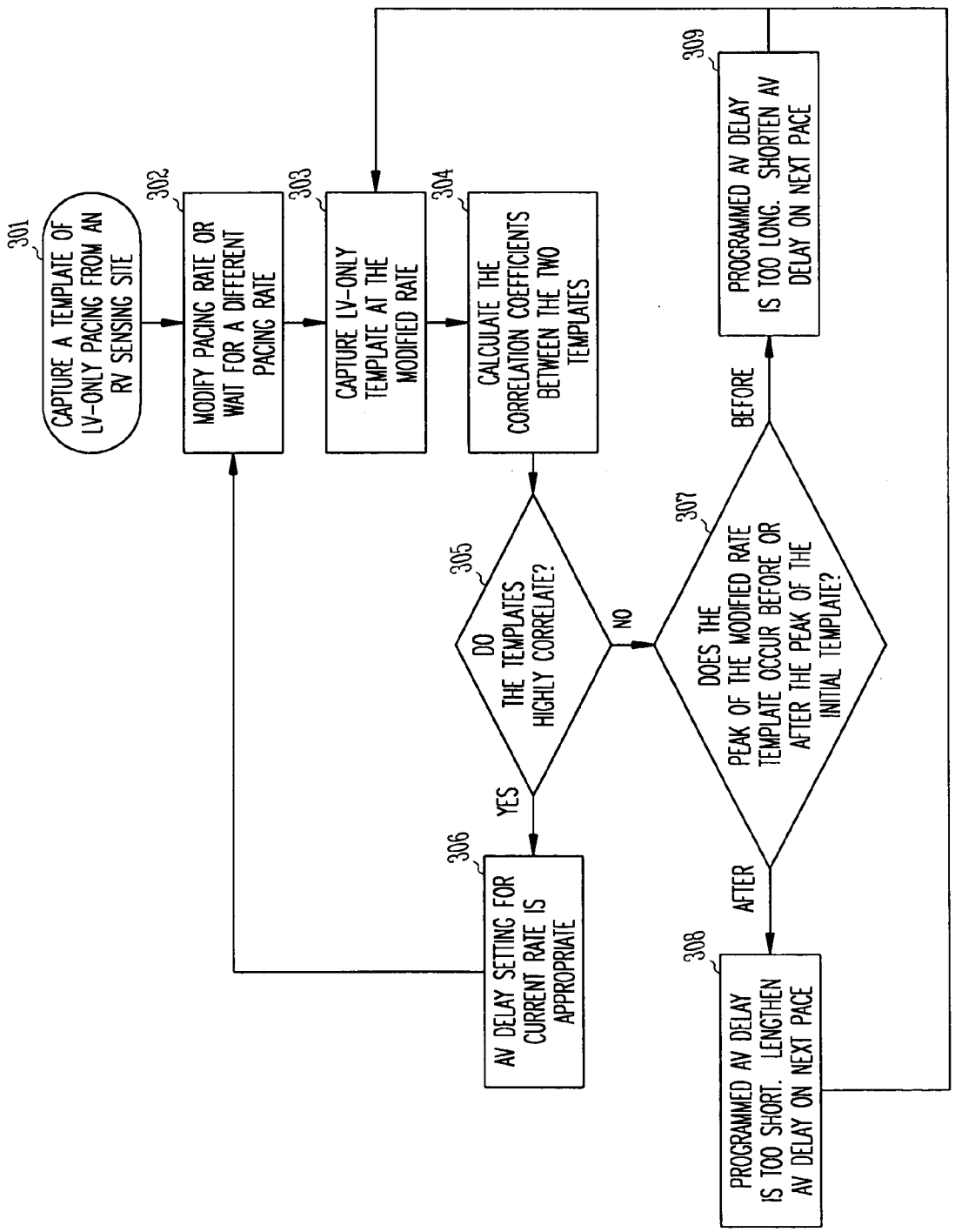
FIGS. 3 and 4 illustrate exemplary algorithms for optimizing the programmed AV delay interval.

FIG. 3 shows a functional flowchart of an algorithm to optimize the dynamic AV delay setting at various rates to maintain ventricular resynchronization or provide an invariant morphology for an autocapture system which may be implemented in the programming of the device controller. The algorithm is illustrated as steps 301 through 309 in the figure. In this example, the pacing mode is changed from BiV to LV mode to analyze the morphology of the evoked response. As explained in the above section, the intrinsic activity of a left bundle branch patient contributes to a large variation of a LV pace when sensed from the right ventricle. It should be noted that a similar analysis could be performed in BiV mode, but the dynamic range and performance of the analysis will be much less than from LV-only pacing. The LV-only template is captured initially at a base rate, for example 60 bpm. As the rate increases, templates are captured at the modified rate and compared with the initial template. If they highly correlate, then the ventricular resynchronization has been maintained at the higher rate. If the templates at different rates do not correlate, then the algorithm examines the relative time of the peaks of the two templates. A peak of the high-rate template occurring before the peak of the low-rate template indicates intrinsic activity occurring in the right ventricle. In this case, the programmed AV delay is too long for the particular ate, so the AV delay value at this particular rate is shortened. Alternatively, a peak of the high-rate template occurring after the peak of the low-rate template indicates a short AV delay value for the particular rate. In this case, the programmed AV delay is lengthened at this rate to maintain ventricular synchronization.

Figure 4:
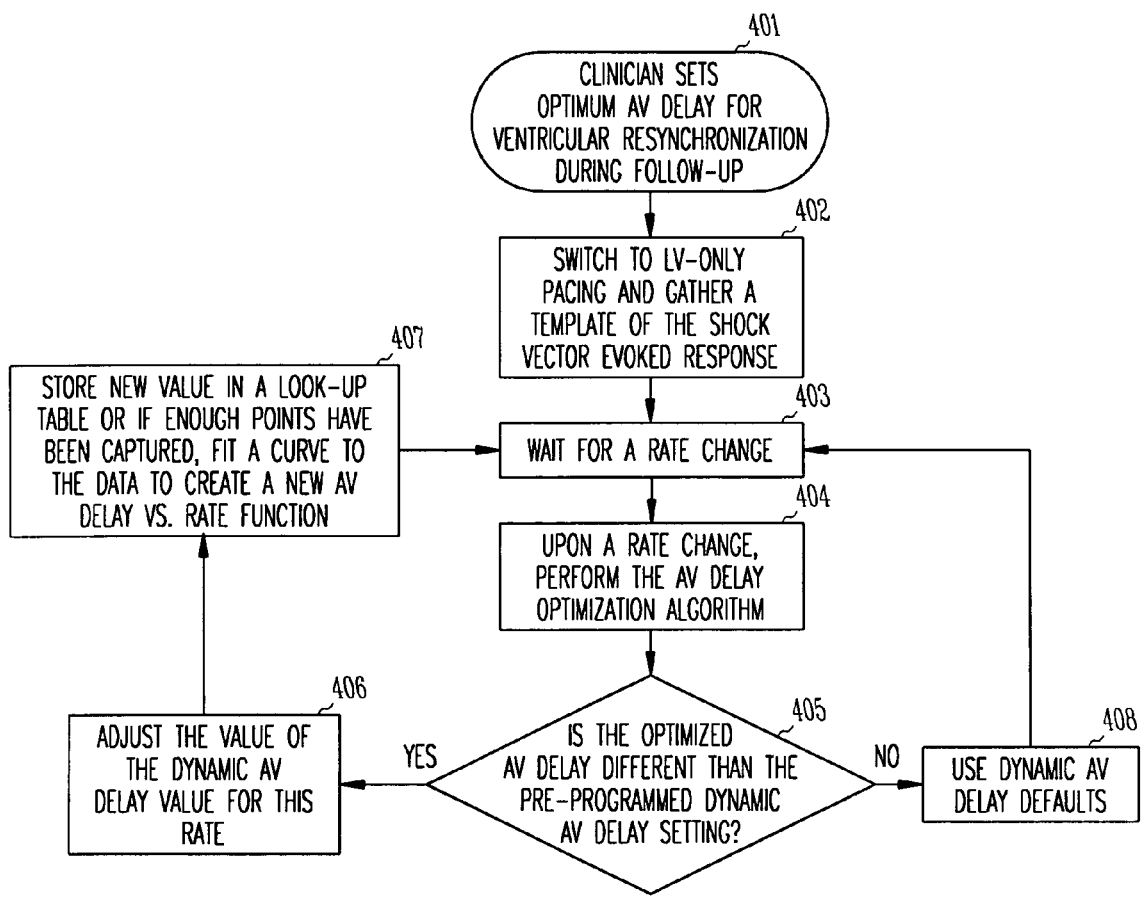

The algorithm described above can be incorporated into the functionality of a heart failure device to supplement the pre-programmed dynamic AV delay algorithm. FIG. 4 shows an example of one such implementation as steps 401 through 408. The clinician first sets the optimum ventricular resynchronization parameters, including the AV delay interval and biventricular offset. The system then switches to LV-only pacing mode to gather an LV-only template at the base rate from the RV shock channel electrogram. The device then returns to normal heart failure therapy until a significant change in rate. Once a suitable rate change has occurred, the pacing output again switches to LV-only pacing for a few beats to gather a template at the higher rate. If there is no change in the morphology, the system defaults to the pre-programmed dynamic AV delay algorithm. If a morphology variation is noted, the system then finds the programmed AV delay value to return the ventricular resynchronization to the optimum settings. The new AV delay value could be stored in an AV delay vs. rate look-up table within the device. Alternatively, once several AV delay values have been found at different rates, a curve could be fitted to these points to develop a new functional expression for AV delay vs. rate (e.g., a linear function). Note that a patient with no RV intrinsic activity would show no variations because of AV delay and would default to the preprogrammed dynamic AV delay function. Once the device determines the optimum AV delay with rate, these values would supplement the preprogrammed dynamic AV delay function. This routine could be repeated at periodic intervals for example once per day, to check for variations from heart remodeling.

4. Example of Morphology-based Adjustment of Pacing Mode

If a biventricular pace is delivered near the intrinsic AV delay, one of the pace pulses may be into tissue which is refractory due to intrinsic activation and, thus, may not be providing any additional resynchronization therapy. Determining if this is occurring by monitoring the evoked response morphology resulting from the programmed pacing provides an opportunity for CRT pacing energy management. For example, after determining whether a BiV pace is providing the same benefit as an RV- or LV-only pace, the implantable device can either recommend to the user to modify pace delivery or the system can automatically change the pace delivery. This determination is done using the programmed parameters that are actual ambulatory settings. The device may also determine whether a BiV pace is providing the same benefit as an RV- or LV-only pace in certain rate ranges (e.g., in rate dependent LBBB). The device can then adjust pace delivery for different zones such as delivering RV-only pacing in one zone (e.g., LRL to x) and BiV pacing in another zone (e.g., x to MPR). This determination could occur during a learning period or a defined treadmill test.

5. Morphology-based Wellness Monitoring

Monitoring the morphology of evoked response electrograms resulting from CRT and recognizing changes to that morphology over time can be useful in providing improved CRT delivery. Such monitoring allows the user to re-optimize pacing parameters or perform some other adjustment to therapy based on analysis of this information. In the case of biventricular pacing, a delivered BiV pace can have various end results which effect the morphology of evoked response electrograms: the BiV pace may capture both ventricles, may capture only the right ventricle, may captures only the left ventricle, or may capture neither ventricle. In addition, measurable differences may occur in evoked response electrograms as the paced AV delay interval nears the intrinsic AV interval. As discussed previously, optimal CRT may require a programmed AV delay interval near the intrinsic AV interval, and there is a need to maintain an optimal AV delay over a wide range of heart rates. The morphology of evoked response electrograms may change either abruptly or gradually over time affecting the end result of a BiV pace using current programmed parameters and compromising optimal CRT. A gradual change in evoked response morphology may be the result of changes in the intrinsic AV interval due to, for example, cardiac remodeling, change in fitness, or change in drug regimen. An abrupt change in evoked response morphology may be the result of a change in drug regimen, silent heart attack, or other incident.

In one implementation of a method for tracking changes in evoked response morphology, the device is programmed such that counts are maintained of BiV capture, RV-only capture on a BiV pace, LV-only capture on a BiV pace, intrinsic excitation of the right or left ventricle where the pace is delivered during the refractory period, fusion events where capture and intrinsic activity occur together, and no capture or excitation of either ventricle. The counts of each event may be further sorted into bins according to the pacing rate which was in operation when the event occurred so that the frequency of occurrence for each type of event can be correlated with pacing rate. Binning against pacing rate in this manner gives a clinician further insight into impact of rate on current CRT programmed parameters. The counts of each type of event may also be compared against a threshold in order to trigger automatic data recording, user notification, or other alarm. Such triggering may occur, for example, when a specified percentage of events are not BiV captures, when a specified percentage of events are BiV fusion events, when a specified absolute number of events are not BiV captures, or when a specified absolute number of events are fusion events. The user may want to re-optimize pacing parameters or perform some other adjustment to therapy based on an analysis of this system feedback. The information obtained in this manner thus improves a physician's ability to evaluate the long-term effectiveness of current CRT programmed parameters and alerts a physician to the possible loss of CRT. The device may also be programmed to make operating adjustments automatically in response to the gathered information.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A method for operating a cardiac rhythm management device in a patient, comprising:

delivering paces to both right and left ventricles in accordance with a programmed biventricular pacing mode, such that the paces are delivered at a programmed biventricular offset interval and after a programmed AV delay interval with respect to an atrial event;

switching to LV-only pacing mode and recording an evoked response test electrogram during an LV-only pace with the programmed AV delay interval;

comparing the test electrogram to an evoked response template electrogram previously recorded during LV-only pacing when the programmed AV delay interval was known to be matched to the patient's then existing intrinsic AV interval;
adjusting the programmed AV delay interval to match the patient's current intrinsic AV interval based upon the comparison of the test and template electrograms;
returning to the biventricular pacing mode with the adjusted AV delay interval.

2. The method of claim 1 wherein the test electrogram is recorded from a right ventricular sensing channel.

3. The method of claim 2 wherein the comparing of the test and template electrograms further comprises:
determining when peaks in the test and template electrograms occur relative to the pace;
shortening the programmed AV delay interval if the peak in the test electrogram occurs earlier than the peak in the template; and,
lengthening the programmed AV delay interval if the peak in the test electrogram occurs later than the peak in the template.

4. The method of claim 1 further comprising determining matched programmed AV delay intervals at a plurality of different pacing rates.

5. The method of claim 4 further comprising:
using the matched AV delay intervals as determined at the plurality of pacing rates may to form a mapping function which maps particular pacing rates to particular programmed AV delay intervals; and,
automatically adjusting the programmed AV delay interval according to the mapping function as the pacing rate changes.

6. The method of claim 5 wherein the mapping function is a look-up table.

7. The method of claim 5 wherein the mapping function is a linear function.

8. A method for operating a cardiac rhythm management device in a patient, comprising:
delivering paces to both right and left ventricles in accordance with a programmed biventricular pacing mode, such that the paces are delivered at a programmed biventricular offset interval and after a programmed AV delay interval with respect to an atrial event;
upon a change by a specified amount in a current pacing rate at which the right and left ventricular paces are delivered, adjusting the programmed AV delay interval according to a mapping function which maps a particular pacing rate to a particular AV delay interval;
switching to LV-only pacing mode and recording an evoked response test electrogram during an LV-only pace with the programmed AV delay interval;
comparing the test electrogram to an evoked response template electrogram previously recorded during LV-only pacing when the programmed AV delay interval was known to be matched to the patient's then existing intrinsic AV interval;
if the test and template electrograms do not sufficiently correlate, adjusting the mapping function so that the programmed AV delay interval which is mapped to by the current pacing rate matches the patient's current intrinsic AV interval based upon the comparison of the test and template electrograms; and
returning to the biventricular pacing mode with the adjusted mapping function.

9. The method of claim 8 wherein the test electrogram is recorded from a right ventricular sensing channel and the comparing of the test and template electrograms further comprises:
determining when peaks in the test and template electrograms occur relative to the pace;
shortening the mapped to AV delay interval if the peak in the test electrogram occurs earlier than the peak in the template; and,
lengthening the mapped to AV delay interval if the peak in the test electrogram occurs later than the peak in the template.

10. The method of claim 8 further comprising recording the test electrogram and comparing the test electrogram with the template electrogram only at periodic intervals.

11. A cardiac rhythm management device, comprising:
pacing channels through which paces may be delivered to both right and left ventricles;
a controller programmed to deliver the paces in accordance with a programmed biventricular pacing mode at a programmed biventricular offset interval and after a programmed AV delay interval with respect to an atrial event;
wherein the controller is programmed to:
switch to an LV-only pacing mode and record an evoked response test electrogram during an LV-only pace;
compare the test electrogram to an evoked response template electrogram previously recorded during LV-only pacing when the programmed AV delay interval was known to be matched to the patient's then existing intrinsic AV interval;
adjust the programmed AV delay interval to match the patient's current intrinsic AV interval based upon the comparison of the test and template electrograms; and,
return to the biventricular pacing mode with the adjusted AV delay interval.

12. The device of claim 11 wherein the test electrogram is recorded from a right ventricular sensing channel.

13. The device of claim 12 wherein the controller is programmed to compare the test and template electrograms by:
determining when peaks in the test and template electrograms occur relative to the pace;
shortening the programmed AV delay interval if the peak in the test electrogram occurs earlier than the peak in the template; and,
lengthening the programmed AV delay interval if the peak in the test electrogram occurs later than the peak in the template.

14. The device of claim 11 wherein the controller is programmed to determine matched programmed AV delay intervals at a plurality of different pacing rates.

15. The device of claim 14 wherein the controller is programmed to:
use the matched AV delay intervals as determined at the plurality of pacing rates may to form a mapping function which maps particular pacing rates to particular programmed AV delay intervals; and,
automatically adjust the programmed AV delay interval according to the mapping function as the pacing rate changes.

16. The device of claim 15 wherein the mapping function is a look-up table.

17. The device of claim 15 wherein the mapping function is a linear function.

18. A cardiac rhythm management device, comprising:
pacing channels through which paces may be delivered to both right and left ventricles;
a controller programmed to deliver the paces in accordance with a programmed biventricular pacing mode at a programmed biventricular offset interval and after a programmed AV delay interval with respect to an atrial event;

wherein the controller is programmed to:

upon a change by a specified amount in a current pacing rate at which the right and left ventricular paces are delivered, adjust the AV delay interval according to a mapping function which maps a particular pacing rate to a particular AV delay interval;

switch to LV-only pacing mode and recording an evoked response test electrogram during an LV-only pace;

compare the test electrogram to an evoked response template electrogram previously recorded during LV-only pacing when the programmed AV delay interval was known to be matched to the patient's then existing intrinsic AV interval;

if the test and template electrograms do not sufficiently correlate, adjust the mapping function so that the programmed AV delay interval which is mapped to by the current pacing rate matches the patient's current intrinsic AV interval based upon the comparison of the test and template electrograms; and return to the biventricular pacing mode with the adjusted mapping function.

19. The device of claim 18 wherein the test electrogram is recorded from a right ventricular sensing channel and the controller is programmed to compare the test and template electrograms and adjust the mapping function by:

determining when peaks in the test and template electrograms occur relative to the pace;

shortening the mapped to AV delay interval if the peak in the test electrogram occurs earlier than the peak in the template; and, lengthening the mapped to AV delay interval if the peak in the test electrogram occurs later than the peak in the template.

20. The device of claim 18 wherein the controller is programmed to record the test electrogram and comparing the test electrogram with the template electrogram only at periodic intervals.

* * * * *